United States Patent [19]

Salce et al.

[11] Patent Number: 5,520,909
[45] Date of Patent: May 28, 1996

[54] METHOD OF PERMANENTLY RESTRUCTURING CURLED OR FRIZZY HAIR

[75] Inventors: Ludwig Salce, Greenwich; Ronald F. Verdi, Norwalk, both of Conn.

[73] Assignee: Conair Corporation, Stamford, Conn.

[21] Appl. No.: 349,928

[22] Filed: Dec. 6, 1994

[51] Int. Cl.⁶ .................................................. A61K 7/09
[52] U.S. Cl. ................... 424/70.51; 424/704; 424/705
[58] Field of Search ........................... 424/70.4, 70.5, 424/70.51

[56] References Cited

U.S. PATENT DOCUMENTS

| | | | |
|---|---|---|---|
| 3,842,848 | 10/1974 | Karjala | 132/204 |
| 4,982,750 | 1/1991 | Kaitz | 132/204 |
| 5,208,014 | 5/1993 | Dubief et al. | 424/71 |
| 5,223,252 | 6/1993 | Kok et al. | 424/72 |
| 5,277,206 | 1/1994 | Rose et al. | 132/204 |
| 5,294,230 | 3/1994 | Wu et al. | 8/127.51 |
| 5,332,570 | 7/1994 | Bergstrom et al. | 424/72 |

FOREIGN PATENT DOCUMENTS

| | | |
|---|---|---|
| 1263318 | 11/1989 | Canada . |
| 57-62217 | 4/1982 | Japan . |
| 63-146808 | 6/1988 | Japan . |

*Primary Examiner*—Jyothsna Venkat
*Attorney, Agent, or Firm*—Haynes N. Johnson

[57] ABSTRACT

A hair relaxant and process in which water-soluble disulfides are added to water-soluble mercaptans, used as reducing agents, to shift the equilibrium point of the relaxer toward the reactants sufficiently such that the relaxant will not cause damage to the hair. The ingredients are carried in a viscous creme base, and there is an absence of sulfite and bisulfite salts. This is followed by rinsing and the use of an oxidizing neutralizer. The process is carried out in the absence of added heat.

13 Claims, No Drawings

METHOD OF PERMANENTLY RESTRUCTURING CURLED OR FRIZZY HAIR

FIELD OF THE INVENTION

This invention relates to the field of hair treatment, and, in particular, to chemical treatment to achieve curl relaxation and/or hair straightening.

BACKGROUND OF THE INVENTION

Permanent restructuring of keratin hair fiber is a two stage process. The first step involves cleavage of the keratin cystine disulfide bond, while the second step involves the reformation of these bonds in a new configuration. This methodology has been used for both perming (i.e., adding curl to straight hair) and relaxing (i.e., removing or modifying curled hair). In the former case, a reducing agent (mercaptan) is used to cleave the cystine disulfide bond while in the latter case a strong alkali or reducing agent (sodium hydroxide, guanidine carbonate or mercaptan) is used. Mercaptan reducing agents, such as salts, esters and amides of thioglycolic, thiolactic, cysteine, etc., are often used as well as other mercaptans, such as cysteamine, thioglycerine, etc., and their derivatives. The use of strong alkalies such as sodium and potassium hydroxide, as well as guanidine carbonate, cleave disulfide bonds by a different chemical mechanism than mercaptans and are used exclusively for removal/modification and not for formation of curls.

Permanent waving of human hair is achieved by placing stress on the hair fiber by winding the fiber on a mandrel. The diameter of the resulting curl will be directly proportional to the diameter of the mandrel employed. A waving lotion containing a water soluble mercaptan is applied to cleave the cystine bonds which will relieve some of the fiber's stress. After rinsing, an oxidant, such as hydrogen peroxide, sodium bromate, or sodium chlorite is then applied to reform the disulfide (i.e., cystine) bonds in the new curled configuration.

Relaxation or modification of curled hair can be achieved by winding tightly curled hair onto mandrels having large diameters and treating the hair with mercaptans as described above. Another methodology is to apply a mercaptan or a strong alkaline chemical (i.e., lye, guanidine carbonate), formulated into a viscous creme base, onto the hair. This viscous creme product is usually applied with a brush and then carefully spread using a comb. Continuous combing action places stress on the curled hair, and the viscous creme holds it in a relatively straight configuration as the cystine disulfide bonds are being chemically cleaved. When the desired "curl-less" configuration is achieved, the alkaline treated hair, which does not require oxidative neutralization, is rinsed with water and washed with an acidic shampoo while the mercaptan treated hair is neutralized with a semi-viscous creme oxidant, such as hydrogen peroxide, sodium bromate, etc. Continuous combing during the neutralization process is necessary so as to maintain the hair in a straight configuration during disulfide bond reformation. When neutralization is complete, in approximately five minutes, the hair is rinsed with water. Either treatment will modify/remove curl from hair fibers.

The prior art includes Kaitz U.S. Pat. No. 4,982,780, which requires eight steps including a heat treatment using a heat-generating composition; Wu et al. U.S. Pat. No. 5,294,230 which uses a waving lotion containing sulfite, bisulfite, or hydrosulfite, together with a water-soluble mercaptan; and Rose et al. U.S. Pat. No. 5,277,206 in which diammonium dithiodiglycolate is applied as a separate "pre-fixation" step before peroxide neutralization.

BRIEF SUMMARY OF THE INVENTION

The present invention provides an improvement in chemical curl relaxation and/or hair straightening. The process can be applied to naturally curly, permed, frizzy, or humidity-susceptible hair. In addition, the condition of chemically treated hair (i.e., tinted hair) can also be improved upon treatment with the proposed invention.

In general, the existing relaxation or hair straightening chemical compositions cause substantial hair damage in addition to scalp irritation. However, the formulas of our invention, while remarkably effective, are exceptionally mild when compared to those normally used to relax hair. The methodology employed requires only three steps: application of relaxing creme formula, rinsing, and neutralization; and it does not require application of heat or heat generating composition.

We have found that the combination of a water soluble mercaptan and diammonium dithiodiglycolate, or other dithio compound, formulated without sulfite or bisulfite in a unique creme base can relax naturally curly, permed, or frizzy and humidity-susceptible hair with practically no hair fiber damage. It does this because the dithio compound shifts the equilibrium point of the relaxing reaction toward the reactants sufficiently to avoid this damage.

In the present invention, diammonium dithiodiglycolate, or another dithio compound, combined with a water soluble mercaptan (i.e., reducing agent), is an active and necessary component of the relaxation chemistry involved, and does not require a separate "pre-fixation" step. Addition of diammonium dithiodiglycolate, or any water soluble disulfide (such as cystine, diammonium dithiodilactate, or cystamine) prevents the over-processing of hair which occurs with the use of many chemical formulations utilized for the relaxation of human hair.

It has been found that our methodology of using a viscous creme eliminates the need to use the "straight Perm Boards" normally required to maintain the hair in a straight configuration during the chemical relaxation procedure.

DETAILED DESCRIPTION OF THE INVENTION

The two step reduction of human hair can be summarized by the equilibrium described in equation I $$KSSK + 2RSH \rightleftharpoons 2KSH + RSSR \qquad (I)$$

Where KSSK represents hair keratin disulfide (i.e., cystine), RSH is a water soluble mercaptan, KSH is reduced keratin, and RSSR is the disulfide of the mercaptan. Since this is a mobile equilibrium reaction, the addition of a disulfide (i.e., RSSR=diammonium dithiodiglycolate or other water soluble disulfides) will force the equilibrium to the left (i.e., toward the reactants KSSK and RSH). The reversibility and high mobility of this reaction will result in relaxation of fiber stress (curl stress) without major reduction of keratin disulfide bonds, that is, with minimum KSH formation.

The addition of exogenous disulfides insures minimal KSH generation by shifting the equilibrium toward the reactants while allowing continuous bond rearrangement (i.e., sulfide-disulfide interchange) resulting in fiber relaxation. The exogenous disulfide used does not have to be derived from the reducing mercaptan but can be any water soluble disulfide or mixed disulfide, such as cystine, cystamine, dithiodiglycolic acid, or dithiodilactic acid.

When the desired relaxation is achieved, the product is rinsed from the hair and the remaining reduced keratin bonds (KSH) are re-oxidized to disulfide bonds to permanently terminate the reversible reaction as described in Equation II:

$$2KSH + H_2O_2 \rightarrow KSSK + 2H_2O \quad (II)$$

In addition, our formulation has been found to improve the texture of hair that has been damaged by previous chemical treatment, such as perming, tinting, highlighting, and environmental exposure. The exact mechanism of this improvement is not known but appears to involve sulfide-disulfide interchange with the exogenous disulfide resulting in mixed disulfide formation. Reduced keratin (KSH) can react with the exogenous disulfide (RSSR or RSSR') to form a keratin mixed disulfide as shown in Equation III:

$$KSH + RSSR \rightleftharpoons KSSR(R') + RSH \quad (III)$$

The keratin mixed disulfide will increase fiber weight and so will augment hair "body" and enhance physical appearance. Hair that has been relaxed with our formulations is in excellent condition and can be re-curled with a conventional perm lotion, or colored, on the same day as the relaxation treatment.

FORMULATIONS (a) The Relaxing Agent

The addition of a water soluble disulfide to a water soluble mercaptan, formulated in a viscous creme base, has been found to relax curled hair and tame frizzy and humidity-susceptible hair, while leaving the hair in exquisite condition.

The dithio compound should be added at a concentration ranging from about 1 to about 9 percent by weight, preferably 3 to 6 percent, depending on the water soluble mercaptan used as the reducing reagent and the pH of the relaxer. As the reactivity ($pK_{SH}$) of the mercaptan increases, at a fixed pH, a higher concentration of dithio is required. In a similar manner, for a fixed mercaptan, the concentration of dithio must be increased as the pH increases. If the concentration of dithio compound is too high for a specific mercaptan and pH, the equilibrium reaction indicated by Equation I will be shifted to the left, toward KSSK and RSH, and insufficient KSH will be present to participate in sulfide-disulfide interchange, resulting in diminished fiber relaxation, within a reasonable time (less than 30 minutes). If the concentration of dithio compound is too low for a specific mercaptan and pH, the equilibrium reaction of Equation I will be shifted to the right, toward KSH and RSSR, resulting in higher concentration of the KSH, which will participate in excessive sulfide-disulfide interchange, resulting in increased undesired hair damage.

If the pH of the formulation is in the 8.5 to 9.0 range, the preferable concentration of the dithio should be in the 3 to 4 percent range. On the other hand, if the pH of the formulation is in the 9.0 to 9.5 range, the preferable dithio concentration should be in the 4 to 6 percent range.

The ratio of mercaptan to dithio can vary from about 9 to one to about one to one, but is preferably in the range of 2 or 3 to one. The exogenous disulfide added (i.e., diammonium dithiodiglycolate [RSSR]) does not have to be derived from the reducing mercaptan (i.e., ammonium thioglycolate [RSH]) but can be any unrelated water soluble disulfide (i.e., cystine, cystamine, dithiodilactic acid, dithiodipropionic acid, etc.).

The mercaptan reducing agent (i.e., ammonium or ethanolamine salts of thioglycolic, thiolactic and mercaptosuccinic acids and their derivatives, as well as cysteamine, cysteine, thioglycerine, etc.), or a mixture of reducing agents (i.e., ammonium thioglycolate plus ammonium thiolactate, ammonium thiolactate plus cysteine, ammonium thioglycolate plus cysteamine, etc.) can be incorporated into a viscous creme base containing a long chain fatty alcohol (i.e., cetearyl alcohol), surfactant (i.e., sodium lauryl sulfate), emulsifying agent (i.e., laureth-23), conditioners (i.e., quaternaries such as olealkonium chloride), pH adjuster (i.e., ammonium hydroxide, monoethanolamine, disodium phosphate, tris (2-hydroxymethyl) aminomethane, etc.), mineral oil, fragrance. The viscosity should be in the 15,000 to 80,000 centipoise range with a preferred range of 30,000 to 60,000, since substantial viscosity is required to maintain the treated hair in the desired configuration during the relaxation treatment.

Six different formulations for relaxing agents are set forth as Examples 1–6 in the Examples. To prepare them the quantity of water indicated is placed into a glass or passivated stainless steel vessel and heated to 75°–80° C. Sodium lauryl sulfate is added and the mixture stirred until a clear solution is obtained. The cetearyl alcohol, laureth-23, and mineral oil are mixed in a separate vessel and heated to 75° C. and stirred until clear. This latter mixture is then slowly added, with stirring, to the sodium lauryl aqueous solution, previously prepared. The mixture is slowly cooled to 45°–50° C. and the remainder of the formula ingredients are added in the order listed in the Examples. Stirring is continued until a homogenous mixture is obtained, and it is then cooled to ambient temperature. Viscosity of these examples should be in the 30,000 to 60,000 centipoise range.

(b) The Neutralizer

A typical semi-viscous neutralizer for this invention will contain aqueous hydrogen peroxide in the range of 1 to 5 percent, with a preferred range of 2 to 3 percent (See Example 7). The neutralizer semi-viscous formulation should also contain the following, or similar, ingredients: surfactant (i.e., sodium lauryl sulfate), long chain fatty alcohol (i.e., cetearyl alcohol), emulsifying agent (i.e., ceteth-20 or laureth-23), conditioner/anti-stat (i.e., olealkonium chloride), pH adjuster (i.e., phosphoric acid), buffering agent (i.e., disodium phosphate), mineral oil, and preservative (i.e., methylparaben). The viscosity range should be in the 1,000 to 6,000 centipoise range, with a preferred range of 2,000 to 6,000.

Formulation of the neutralizer is set forth in Example 7 of the Examples. To prepare it, the indicated water is placed in a glass or passivated stainless steel vessel and heated to 75°–80° C. Methylparaben, sodium lauryl sulfate and disodium phosphate are added, and the mixture is stirred until a clear solution is obtained. The cetearyl alcohol, laureth-23, and mineral oil are mixed in a separate vessel, heated to 75° C. and stirred until clear. This latter phase is slowly added, with stirring, to the aqueous solution containing the methyl paraben, sodium lauryl sulfate, and disodium phosphate. When the addition is complete, the mixture is cooled to 35°–40° C. and the hydrogen peroxide, phosphoric acid, and olealkonium chloride are added. Stirring is continued until a homogenous mixture is obtained, and it is then cooled to ambient temperature. Viscosity of this neutralizer should be in the 1,000 to 6,000 centipoise range.

EXAMPLES

In order to test the efficacy of the present invention, live models with natural, curly, permed, frizzy, or humidity-susceptible hair were treated with the formulations described in Examples 1–6 (See table of Examples).

The methodology employed was as follows: The model's hair was shampooed and dried with a towel until damp. After combing the hair thoroughly, it was sectioned into "T" partings. Sectioning at the nape of the neck, the relaxer was applied to ¾" sections across the head with a "tinting" brush. The hair was then combed thoroughly with medium tension to achieve a straight look. This procedure was continued up to the top of the head while combing each section and making sure that there was enough relaxer on the hair at all times to keep the hair moist with relaxer. The hair was continuously combed in different directions (i.e., from side to side and back and forward) during the processing time, which can vary from five to twenty-five minutes, depending upon the texture, porosity and type of curl to be removed (A permed curl would take 5 to 7 minutes and naturally curly hair 7 to 25 minutes).

After the processing was completed, the hair was rinsed thoroughly for 5 to 7 minutes, depending upon the density of the hair, while maintaining the hair as straight as possible. The excess moisture was squeezed from the hair and the hair was towel blotted to remove excess water.

A semi-viscous neutralizer was then applied in the same manner as the relaxer. After processing for 5 minutes, the neutralizer was removed by rinsing for 3 to 4 minutes. The processed hair was then styled to achieve the desired results.

In all instances, treated hair had considerably less curl than untreated hair and was found to be in excellent condition. The superior condition of the hair allowed it to be permed or colored immediately after completion of the treatment.

In addition, samples of the formulation described in Example 1 were sent to ten independent professionally licensed cosmetologists and evaluated in their salons using the methodology just described. Reported results are summarized in Table I (The number of testers giving each evaluation is given just below the evaluations). These data clearly show the effectiveness and acceptability of the invention.

The examples and other descriptions in this specification are illustrative of our invention and are not to be considered as limitations thereof.

TABLE 1

RELAXER FIELD TEST

| 1 | HAIR COLOR LOSS | MUCH | SOME | NONE |
|---|---|---|---|---|
| | | | 6 | 4 |

| 2 | BODY | LITTLE | SOME | ABUNDANT |
|---|---|---|---|---|
| | | 1 | 6 | 3 |

| 3 | WET HAIR COMB THROUGH | HARSH | GOOD | GREAT |
|---|---|---|---|---|
| | | 1 | 7 | 2 |

| 4 | DRY HAIR MANAGEABILITY | POOR | GOOD | GREAT |
|---|---|---|---|---|
| | | | 4 | 5 |

| 5 | DRY HAIR CONDITION | POOR | GOOD | GREAT |
|---|---|---|---|---|
| | | 1 | 3 | 6 |

| 6 | DRY HAIR COMB THROUGH | HARSH | GOOD | GREAT |
|---|---|---|---|---|
| | | | 5 | 4 |

| 7 | OVERALL HAIR CONDITION | POOR | GOOD | GREAT |
|---|---|---|---|---|
| | | | 4 | 6 |

| 8 | ESTIMATED % CURL REMOVAL | | | | |
|---|---|---|---|---|---|
| | 0 | 25 | 50 | 75 | 100 |
| | | | 1 | 5 | 4 |

| 9 | EASE OF APPLICATION | | | |
|---|---|---|---|---|
| | | RELAXER | DIFFICULT | EASY |
| | | | 1 | 9 |
| | | NEUTRALIZER | DIFFICULT | EASY |
| | | | | 10 |

| 10 | OVERALL RATING | POOR | GOOD | GREAT |
|---|---|---|---|---|
| | | | 4 | 6 |

| INGREDIENT | EXAMPLES | | | | | | |
|---|---|---|---|---|---|---|---|
| | #1 % Wt./Wt. | #2 % Wt./Wt. | #3 % Wt./Wt. | #4 % Wt./Wt. | #5 % Wt./Wt. | #6 % Wt./Wt. | #7 % Wt./Wt. |
| Deionized Water | 62.34 | 60.66 | 51.08 | 50.80 | 63.64 | 53.07 | 92.09 |
| Sodium Lauryl Sulfate | 0.33 | 0.33 | 0.33 | 0.33 | 0.33 | 0.33 | 0.22 |
| Cetearyl Alcohol | 5.63 | 5.63 | 5.63 | 5.63 | 5.63 | 5.63 | 1.26 |
| Laureth-23 | 0.95 | 0.95 | 0.95 | 0.95 | 0.95 | 0.95 | 0.32 |
| Mineral Oil | 0.95 | 0.95 | 0.95 | 0.95 | 0.95 | 0.95 | 0.32 |
| Fragrance | 0.20 | 0.20 | 0.25 | 0.20 | 0.30 | 0.25 | — |
| Ammonium Thioglycolate (60%) | 15.41 | 15.41 | — | — | 15.41 | 13.12 | — |
| Diammonium Dithiodiglycolate (40%) | 10.89 | — | 10.89 | 10.89 | — | 9.45 | — |
| Ammonium Hydroxide (28%) | 3.30 | 3.30 | 4.80 | — | 2.15 | 4.25 | — |
| Diammonium Dithiodipropionate (40%) | — | 12.57 | — | — | — | — | — |
| Cysteine Hydrochloride | — | — | 2.00 | — | — | 2.00 | — |
| Ammonium Thiolactate (40%) | — | — | 23.12 | — | — | 10.00 | — |
| Monoethanolamine Thioglycolate (40%) | — | — | — | 24.50 | — | — | — |
| Monoethanolamine (99%) | — | — | — | 5.75 | — | — | — |
| Cystamine Dihydrochloride | — | — | — | — | 10.64 | — | — |
| Methylparaben | — | — | — | — | — | — | 0.05 |
| Disodium Phosphate | — | — | — | — | — | — | 0.02 |
| Hydrogen Peroxide (50%) | — | — | — | — | — | — | 4.70 |
| Phosphoric Acid | — | — | — | — | — | — | 0.02 |
| Olealkonium Chloride | — | — | — | — | — | — | 1.00 |
| TOTAL | 100.00 | 100.00 | 100.00 | 100.00 | 100.00 | 100.00 | 100.00 |

FORMULAS #1–6 = RELAXERS
FORMULA #7 = NEUTRALIZER

We claim:

1. A method of relaxing hair comprising the steps of applying a water-soluble mercaptan reducing agent to the hair to provide a mercaptan-hair reducing reaction, and water soluble disulfides, but not any sulfite or bisulfite salts, where in said water-soluble mercaptan reducing agent is selected from the amine, group consisting of ammonium salts of thioglycolic acid, ethanolamine salts of thioglycolic acid, thiolactic acid, mercaptosuccinic acid, cysteine, cysteamine, and thioglycerin, said water-soluble disulfide is selected from the group consisting of dithiodiglycolates, dithiodilactates, and dithiodipropionates, the ratio of said water-soluble mercaptan reducing agent to said water-soluble disulfide being between about 9 to 1 and 1 to 1, said water-soluble mercaptan reducing agent being carried by a viscous creme base having a viscosity of between 30,000 and 60,000 centipoise, said water-soluble disulfides being in sufficient quantity to cause the equilibrium point of said mercaptan-hair reducing reaction to be moved toward the reactants, allowing said mercaptan-hair reaction to take place, and thereafter rinsing the hair and applying an oxidizing neutralizer to the hair, whereby the hair is relaxed, but hair damage is reduced.

2. The method of claim 1 in which said water-soluble disulfide is diammonium dithiodiglycolate.

3. The method of claim 1 in which said water-soluble disulfide is diammonium dithiodipropionate.

4. The method of claim 1 in which the pH of said water-soluble mercaptan reducing agent is between 8.5 and 9.0 and in which said water-soluble disulfides are about 3 to 4 percent by weight of said reducing agent.

5. The method of claim 1 in which the pH of said water-soluble mercaptan reducing agent is between 9.0 and 9.5 and in which said water-soluble disulfides are about 4 to 6 percent by weight of said reducing agent.

6. The method of claim 1 in which the ratio of said water-soluble mercaptan reducing agent to said water-soluble disulfide is between three to one and one to one.

7. A relaxing agent for relaxing hair using a mercaptan-hair reducing reaction, said relaxing agent consisting essentially of a water-soluble mercaptan reducing agent is selected from the amine, group consisting of ammonium salts of thioglycolic acid, ethanolamine salts of thioglycolic acid, thiolactic acid, mercaptosuccinic acid, cysteine, cysteamine, and thioglycerin, at least one water-soluble disulfide selected from the group consisting of dithiodiglycolates, dithiodilactates, and dithiodipropionates, the ratio between said water-soluble mercaptan reducing agent and said water-soluble disulfide being between about 9 to 1 and 1 to 1, and a viscous creme base having a viscosity of between 15,000 and 80,000 centipoise, said water-soluble disulfide being in sufficient quantity relative to said water-soluble mercaptan reducing agent to cause the equilibrium point of said mercaptan-hair reaction to be moved toward the reactants, whereby said relaxing agent can be used for relaxing hair and hair damage is reduced.

8. The relaxing agent of claim 7 in which said water-soluble disulfide is diammonium dithiodiglycolate.

9. The relaxing agent of claim 7 in which said water-soluble disulfide is diammonium dithiodipropionate.

10. The relaxing agent of claim 7 in which said viscous creme base has a viscosity of between 30,000 and 60,000 centipoise.

11. The relaxing agent of claim 7 in which the pH is between 8.5 and 9.0 and in which said water-soluble disulfides are about 3 to 4 percent by weight of said relaxing agent.

12. The relaxing agent of claim 7 in which the pH is between 9.0 and 9.5 and in which said water-soluble disulfides are about 4 to 6 percent by weight of said relaxing agent.

13. The relaxing agent of claim 7 in which the ratio of said water-soluble mercaptan reducing agent to said water-soluble disulfide is between three to one and one to one.

* * * * *